United States Patent
Edic et al.

(10) Patent No.: US 7,054,405 B2
(45) Date of Patent: *May 30, 2006

(54) SYSTEM AND METHOD FOR COMPUTING VOLUMETRIC PERFUSION

(75) Inventors: Peter Michael Edic, Albany, NY (US); Melissa Liliane Vass, Milwaukee, WI (US); Anne Marie Conry, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/095,437

(22) Filed: Mar. 31, 2005

(65) Prior Publication Data

US 2005/0169420 A1    Aug. 4, 2005

Related U.S. Application Data

(63) Continuation-in-part of application No. 10/304,380, filed on Nov. 26, 2002, now Pat. No. 6,888,914.

(51) Int. Cl.
*A61B 6/00* (2006.01)
(52) U.S. Cl. .......................... 378/4; 378/901
(58) Field of Classification Search ............ 378/4, 378/8, 19, 62, 95, 98.11, 98.12, 901; 382/130, 382/131, 132; 600/420, 425, 431
See application file for complete search history.

(56) References Cited

U.S. PATENT DOCUMENTS

| | | | | |
|---|---|---|---|---|
| 6,353,653 B1 * | 3/2002 | Edic | ...... | 378/8 |
| 6,480,560 B1 | 11/2002 | Hsieh | ...... | 378/8 |
| 6,628,743 B1 | 9/2003 | Drummond et al. | ...... | 378/8 |
| 6,721,386 B1 | 4/2004 | Bulkes et al. | ...... | 378/8 |
| 6,888,914 B1 * | 5/2005 | Edic | ...... | 378/4 |
| 2004/0077941 A1 | 4/2004 | Reddy et al. | ...... | 600/428 |
| 2004/0082846 A1 | 4/2004 | Johnson et al. | ...... | 600/410 |
| 2004/0111023 A1 | 6/2004 | Edic et al. | ...... | 600/425 |

* cited by examiner

*Primary Examiner*—Courtney Thomas
(74) *Attorney, Agent, or Firm*—Fletcher Yoder

(57) ABSTRACT

A method for computing volumetric perfusion using a computed tomography imaging (CT) system is presented. The method includes irradiating a spatially dynamic object within a field of view of the computed tomography imaging system for requisite view angle positions of the gantry. Furthermore, the method includes operating the computed tomography imaging system in a continuous data acquisition mode to acquire projection data representative of the spatially dynamic object. In addition, the method includes processing the projection data to generate time-resolved projection data. Reconstructions are generated using the time-resolved projection data. Additionally, the method includes computing the volumetric perfusion in the spatially dynamic object using the reconstructed data. Computer-readable medium that afford functionality of the type defined by this method is also contemplated in conjunction with the present technique.

24 Claims, 5 Drawing Sheets

SYSTEM AND METHOD FOR COMPUTING VOLUMETRIC PERFUSION

CROSS REFERENCE TO RELATED APPLICATIONS

This application is a Continuation-in-Part of U.S. patent application Ser. No. 10/304,380, entitled "Methods and Apparatus for Computing Volumetric Perfusion", by Peter Edic et al. filed on Nov. 26, 2002, now U.S. Pat. No. 6,888,914, which is herein incorporated by reference.

BACKGROUND

The invention relates generally to computed tomography (CT) imaging, and more particularly to an apparatus and method for computing volumetric perfusion from temporal reconstructions of tissue attenuation characteristics using digital area detector technology.

As will be appreciated by one skilled in the art, tissue perfusion may be defined as the passage of blood through a volume under consideration. In more specific terms, tissue perfusion may be defined as the flow of blood per unit volume of tissue. Perfusion parameters may include regional blood volume, regional mean transit time, regional blood flow, permeability surface area, and time of arrival. Due to the low contrast of distributed blood volumes in tissues and/or organs, signal-to-noise ratio, dynamic range and frequency resolution in the X-ray detection systems are important factors in systems that perform perfusion imaging. Additionally, another critical factor to consider when computing tissue perfusion is object motion during imaging, which may obscure the low contrast signal.

CT perfusion algorithms may continuously acquire projection data from limited axial coverage of the patient to adequately measure the contrast dynamics, such as uptake and washout of contrast enhancing medium in the tissue or organ being imaged. Multi-row detector technology facilitates the simultaneous acquisition of multiple slices (for example, 16 slices in some systems) of projection data to be acquired, reconstructed, and processed for perfusion evaluation. Such systems may provide adequate temporal sampling of the contrast dynamics of the tissue in spatially stationary organs; however, these systems do not provide the axial coverage to image the whole organ.

CT imaging techniques may present certain challenges when imaging dynamic internal structures or organs, such as the heart. For example, in cardiac imaging, the motion of the heart causes inconsistencies in the projection data, which, after reconstruction, may result in various motion-related image artifacts such as blurring, streaking, or discontinuities. In particular, artifacts may occur during cardiac imaging when projections that are not acquired at the same point in the cardiac cycle, i.e., the same phase, are used to reconstruct the image or images that comprise the volume.

It may therefore be desirable to develop techniques to advantageously enhance the temporal resolution in reconstructed data representative of spatially dynamic and/or temporally dynamic objects, such as for a heart and/or a heart perfused with contrast agent respectively.

BRIEF DESCRIPTION

Briefly in accordance with an exemplary embodiment of the present technique, a method for computing volumetric perfusion using a computed tomography imaging (CT) system is presented. The method includes irradiating a spatially dynamic object within a field of view of the computed tomography imaging system for requisite view angle positions of the gantry. Furthermore, the method includes operating the computed tomography imaging system in a continuous data acquisition mode to acquire projection data representative of the spatially dynamic object. In addition, the method includes processing the projection data to generate time-resolved projection data. Reconstructions are generated using the time-resolved projection data. Additionally, the method includes computing the volumetric perfusion in the spatially dynamic object using the reconstructed data. Computer-readable medium that afford functionality of the type defined by this method is also contemplated in conjunction with the present technique.

According to a further embodiment of the present technique, a CT imaging system for computing volumetric perfusion in a spatially dynamic object is presented. The system includes a radiation source and an area detector. The system also includes a computer operationally coupled to the radiation source and the area detector. The computer is configured to irradiate a spatially dynamic object within a field of view of the computed tomography imaging system for requisite view angle positions of the gantry. The computer also operates the computed tomography imaging system in a continuous data acquisition mode to acquire projection data representative of the spatially dynamic object, processes the projection data to generate time-resolved projection data, generates reconstructions using the time-resolved projection data, and computes the volumetric perfusion in the spatially dynamic object using the reconstructed data.

According to another embodiment of the present technique, a method for computing volumetric perfusion using a CT system is presented. The method includes irradiating a spatially dynamic object within a field of view of the computed tomography imaging system for requisite view angle positions of the gantry. The method also includes operating the computed tomography imaging system in a continuous data acquisition mode to acquire projection data representative of the spatially dynamic object. Furthermore, the method includes identifying projection data corresponding to a predetermined temporal window of cyclic motion of the spatially dynamic object. In addition, the method includes performing a fan-to-parallel rebinning to resample the projection data. Further, the method includes processing the resampled projection data to generate the time-resolved projection data. Reconstructions are generated using the time-resolved projection data. Additionally, the method includes computing the volumetric perfusion in the spatially dynamic object using the reconstructed data.

According to a yet another embodiment of the present technique, a method for computing volumetric perfusion using a CT system is presented. The method includes irradiating a spatially dynamic object within a field of view of the computed tomography imaging system for requisite view angle positions of the gantry. The computed tomography imaging system is operated in a continuous data acquisition mode to acquire projection data representative of the spatially dynamic object in response to an external trigger. The method also includes processing the projection data to generate time-resolved projection data. Reconstructions are generated using the time-resolved projection data. In addition, volumetric perfusion in the spatially dynamic object is computed using the reconstructed data.

DRAWINGS

These and other features, aspects, and advantages of the present invention will become better understood when the following detailed description is read with reference to the accompanying drawings in which like characters represent like parts throughout the drawings, wherein.

Figure 4:
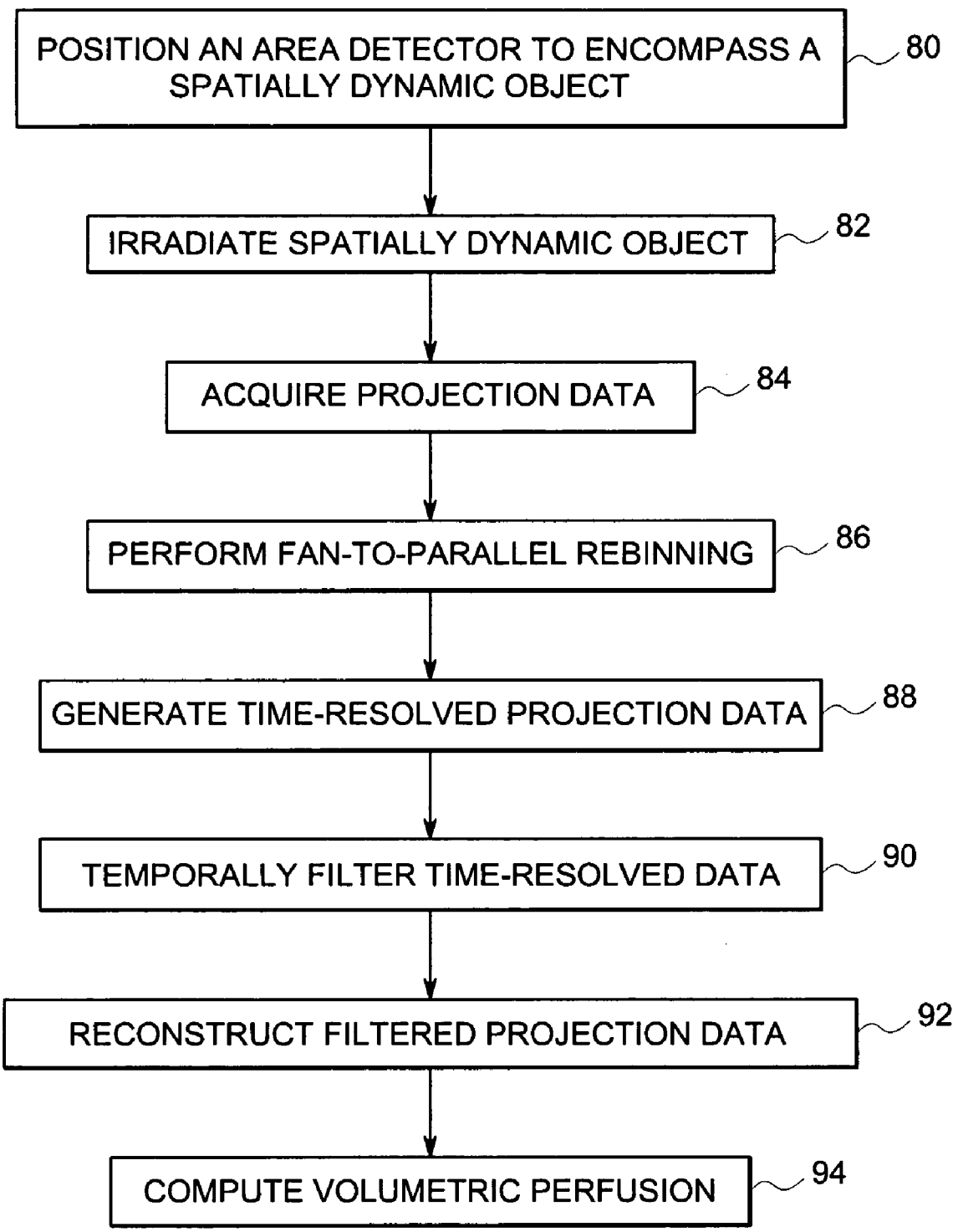
Figure 5:
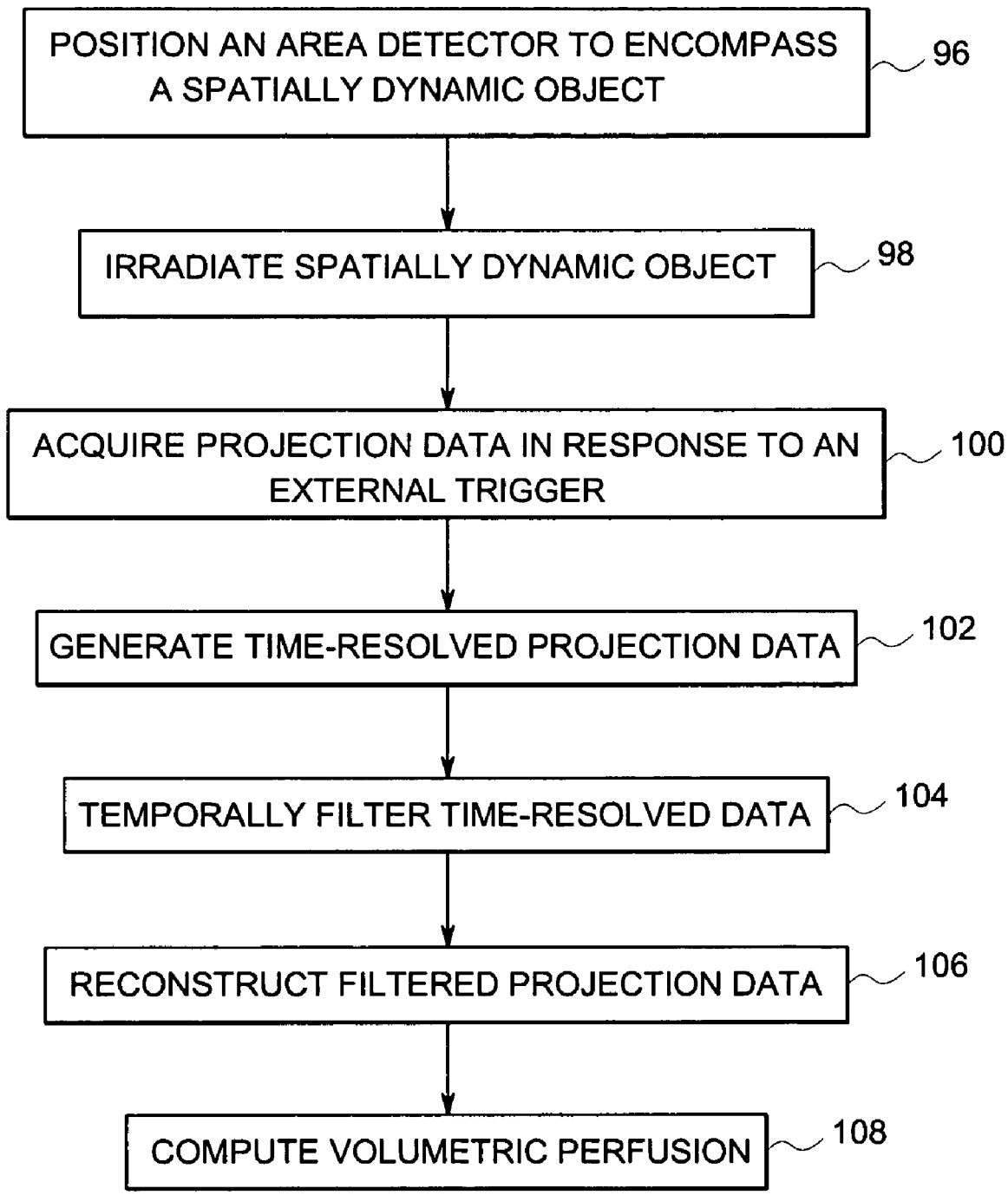

FIG. 4 is a flowchart illustrating another exemplary method for computing volumetric perfusion in a spatially dynamic organ using a CT imaging system, in accordance with aspects of the present technique; and FIG. 5 is a flowchart illustrating yet another exemplary method for computing volumetric perfusion in a spatially dynamic organ using a CT imaging system, in accordance with aspects of the present technique.

DETAILED DESCRIPTION

Imaging spatially dynamic organs poses a challenge because of motion experienced by the organ being imaged. For example, peristalsis, which is an autonomous and vital process, involves a distinctive pattern of smooth muscle contractions that propels foodstuffs distally through the esophagus and intestines. Similarly, motion of organs and structures in the thorax can occur due to breathing. Breath-holds for several minutes are not feasible if a long imaging sequence is necessary. Consequently, either an interrupted imaging sequence allowing several separate breath-holds, which leads to gaps in the acquisition and abrupt step changes in adjoining structures, such as the liver position, or the use of free breathing must be used while the dynamic imaging series is obtained. The use of free breathing is preferred but is currently limited by severe motion artifact. As an additional example, in cardiac imaging, the motion of the heart causes inconsistencies in the projection data, which, after reconstruction, may result in various motion-related image artifacts such as blurring, streaking, or discontinuities. Moreover, temporally varying characteristics of tissue, such as contrast dynamics occurring within a certain finite temporal window, may induce image artifacts such as blurring, streaking, or discontinuities. It may therefore be desirable to circumvent the disadvantages encountered by the current imaging techniques by developing techniques that improve temporal resolution in the projection data used for reconstruction. Additionally, it may also be desirable to reduce noise in either the projection or image data.

Figure 1:
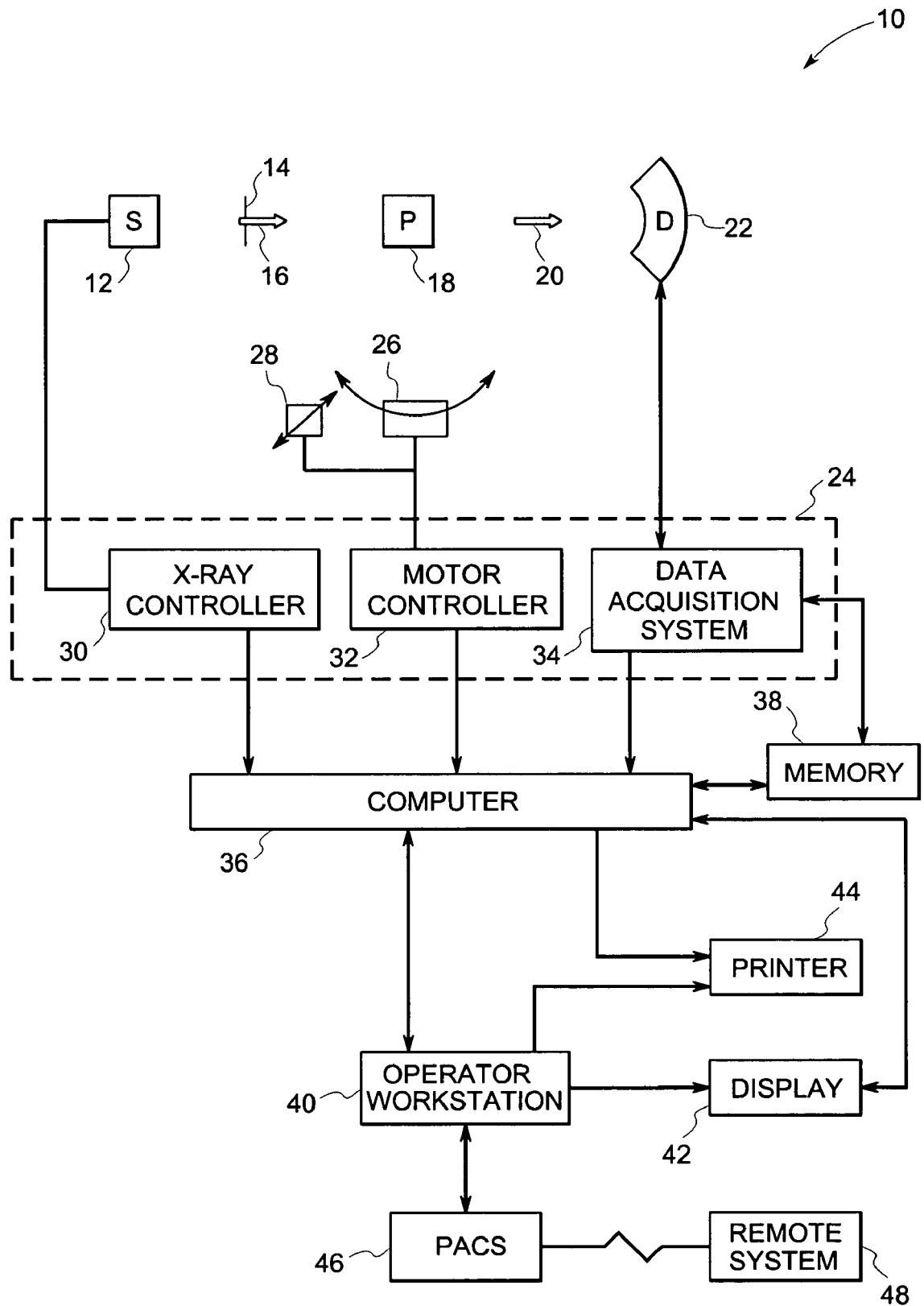
FIG. 1 is a block diagram of an exemplary imaging system in the form of a CT imaging system for use in producing processed images, in accordance with aspects of the present technique.

FIG. 1 is a block diagram showing an imaging system 10 for acquiring and processing image data in accordance with the present technique. In the illustrated embodiment, the system 10 is a computed tomography (CT) system designed to acquire X-ray projection data, to reconstruct the projection data into an image, and to process the image data for display and analysis in accordance with the present technique. In the embodiment illustrated in FIG. 1, the imaging system 10 includes a source of X-ray radiation 12. In one exemplary embodiment, the source of X-ray radiation 12 is an X-ray tube. The source of X-ray radiation 12 may include thermionic or solid-state electron emitters directed at an anode to generate X-rays or, indeed, any other emitter capable of generating X-rays having a spectrum and energy useful for imaging a desired object. Examples of suitable electron emitters include tungsten filament, tungsten plate, field emitter, thermal field emitter, dispenser cathode, thermionic cathode, photo-emitter, and ferroelectric cathode.

The source of radiation 12 may be positioned near a collimator 14, which may be configured to shape a stream of radiation 16 that is emitted by the source of radiation 12. The stream of radiation 16 passes into the imaging volume containing the subject to be imaged, such as a human patient 18. The stream of radiation 16 may be generally fan-shaped or cone-shaped, depending on the configuration of the detector array, discussed below, as well as the desired method of data acquisition. A portion 20 of radiation passes through or around the subject and impacts a detector array, represented generally at reference numeral 22. Detector elements of the array produce electrical signals that represent the intensity of the incident X-ray beam. These signals are acquired and processed to reconstruct an image of the features within the subject.

The radiation source 12 is controlled by a system controller 24, which furnishes both power, and control signals for CT examination sequences. Moreover, the detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, the system controller 24 is coupled via a motor controller 32 to a rotational subsystem 26 and a linear positioning subsystem 28. In one embodiment, the rotational subsystem 26 enables the X-ray source 12, the collimator 14 and the detector 22 to be rotated one or multiple turns around the patient 18. In other embodiments, the rotational subsystem 26 may rotate only one of the source 12 or the detector 22 or may differentially activate various stationary electron emitters to generate X-ray radiation and/or detector elements arranged in a ring about the imaging volume. In embodiments in which the source 12 and/or detector 22 are rotated, the rotational subsystem 26 may include a gantry. Thus, the system controller 24 may be utilized to operate the gantry. The linear positioning subsystem 28 enables the patient 18, or more specifically a patient table, to be displaced linearly. Thus, the patient table may be linearly moved within the gantry to generate images of particular areas of the patient 18.

Additionally, as will be appreciated by those skilled in the art, the source of radiation 12 may be controlled by an X-ray controller 30 disposed within the system controller 24. Particularly, the X-ray controller 30 is configured to provide power and timing signals to the X-ray source 12.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a computer 36.

The computer 36 typically is coupled to or incorporates the system controller 24. The data collected by the data acquisition system 34 may be transmitted to the computer 36 for subsequent processing and reconstruction. The computer 36 may comprise or communicate with a memory 38 that can store data processed by the computer 36 or data to be processed by the computer 36. It should be understood that any type of memory configured to store a large amount of data might be utilized by such an exemplary system 10. Moreover, the memory 38 may be located at the acquisition system or may include remote components, such as network accessible memory media, for storing data, processing parameters, and/or routines for implementing the techniques described below.

The computer 36 may also be adapted to control features such as scanning operations and data acquisition that may be enabled by the system controller 24. Furthermore, the computer 36 may be configured to receive commands and scanning parameters from an operator via an operator workstation 40, which is typically equipped with a keyboard and other input devices (not shown). An operator may thereby control the system 10 via the input devices. Thus, the operator may observe the reconstructed image and other data relevant to the system from computer 36, initiate imaging, and so forth.

A display 42 coupled to the operator workstation 40 may be utilized to observe the reconstructed images. Additionally, the scanned image may also be printed by a printer 44, which may be coupled to the operator workstation 40. The display 42 and printer 44 may also be connected to the computer 36, either directly or via the operator workstation 40. The operator workstation 40 may also be coupled to a picture archiving and communications system (PACS) 46. It should be noted that PACS 46 might be coupled to a remote system 48, such as radiology department information system (RIS), hospital information system (HIS) or to an internal or external network, so that others at different locations may gain access to the image data.

It should be further noted that the computer 36 and operator workstation 40 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, a virtual private network or the like.

Figure 2:
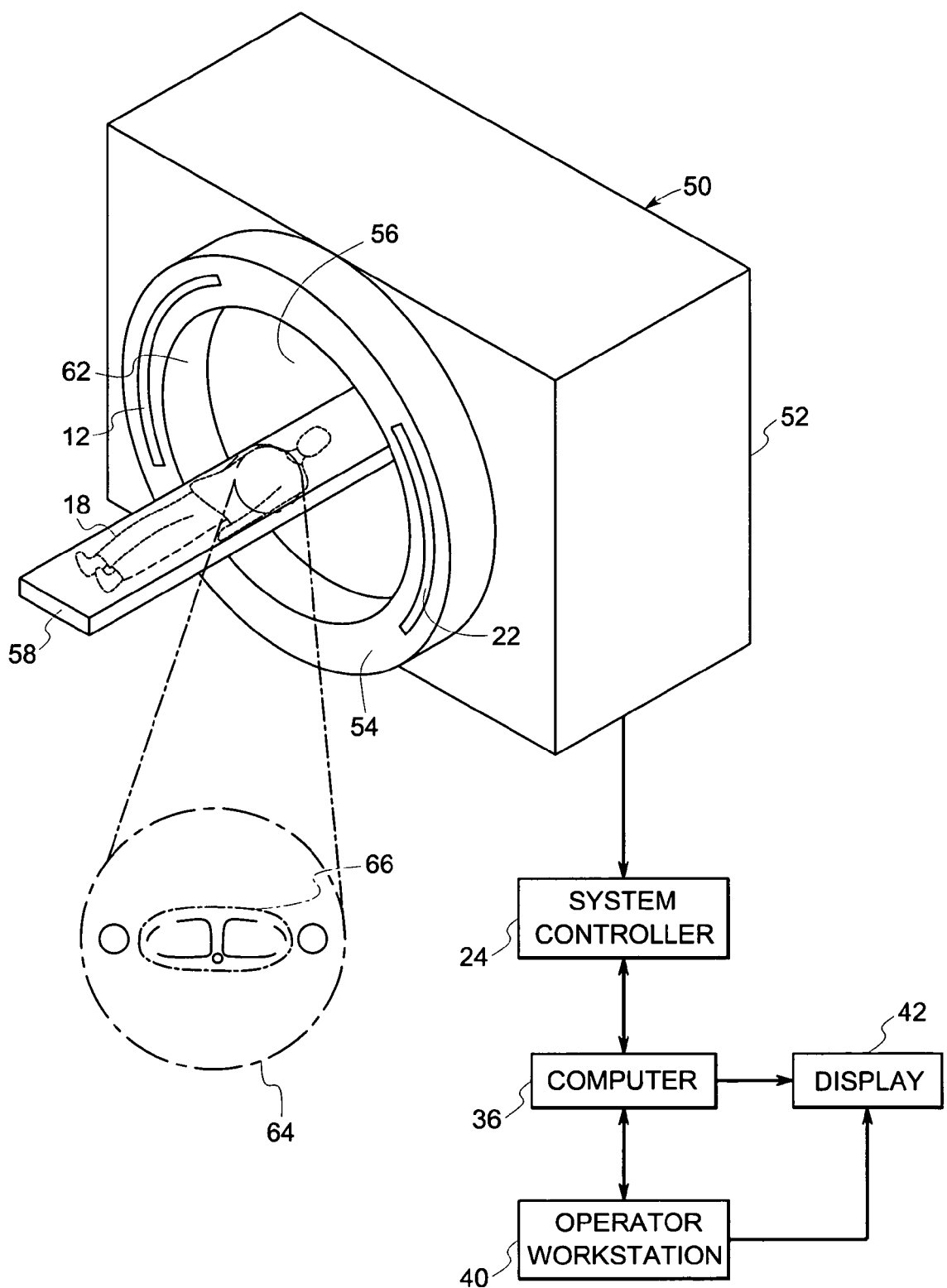
FIG. 2 is a block diagram of a physical implementation of the CT system of FIG. 1, in accordance with aspects of the present technique.

As noted above, an exemplary imaging system utilized in a present embodiment may be a CT scanning system 50, as depicted in greater detail in FIG. 2. The CT scanning system 50 may be a multi-slice CT (MSCT) system that offers a wide array of axial coverage, high rotational speed of the gantry, and high spatial resolution. Alternately, the CT scanning system 50 may be a volumetric CT (VCT) system utilizing a cone-beam geometry and an area detector to allow the imaging of a volume, including such as an entire internal organ of a subject, at high or low gantry rotational speeds. The CT scanning system 50 is illustrated with a frame 52 and a gantry 54 that has an aperture 56 through which a patient 18 may be moved. A patient table 58 may be positioned in the aperture 56 of the frame 52 and the gantry 54 to facilitate movement of the patient 18, typically via linear displacement of the table 58 by the linear positioning subsystem 28 (see FIG. 1). The gantry 54 is illustrated with the source of radiation 12, such as an X-ray tube that emits X-ray radiation from a focal point 62. For cardiac imaging, the stream of radiation is directed towards a cross section of the patient 18 including the heart.

In typical operation, the X-ray source 12 projects an X-ray beam from the focal point 62 and toward detector array 22. The collimator 14 (see FIG. 1), such as lead or tungsten shutters, typically defines the size and shape of the X-ray beam that emerges from the X-ray source 12. The detector 22 is generally formed by a plurality of detector elements, which detect the X-rays that pass through and around a subject of interest, such as the heart or chest. Each detector element produces an electrical signal that represents the intensity of the X-ray beam at the position of the element during the time the beam strikes the detector. The gantry 54 is rotated around the subject of interest so that a plurality of radiographic views may be collected by the computer 36.

Thus, as the X-ray source 12 and the detector 22 rotate, the detector 22 collects data related to the attenuated X-ray beams. Data collected from the detector 22 then undergoes pre-processing and calibration to condition the data to represent the line integrals of the attenuation coefficients of the scanned objects. The processed data, commonly called projections, may then be filtered and backprojected to formulate an image of the scanned area. A formulated image may incorporate, in certain modes, projection data for less or more than 360 degrees of rotation of the gantry 54.

Once reconstructed, the image produced by the system of FIGS. 1 and 2 reveals internal features 66 of the patient 18. In traditional approaches for the diagnosis of disease states, and more generally of medical conditions or events, a radiologist or physician would consider the reconstructed image 64 to discern characteristic features of interest. In cardiac imaging, such features 66 include coronary arteries or stenotic lesions of interest, and other features, which would be discernable in the image, based upon the skill and knowledge of the individual practitioner. Other analyses may be based upon capabilities of various CAD algorithms.

Reconstruction of images 64 of dynamically moving tissue may present particular concerns. Projection data sets that encompass data points acquired at different phases of the cardiac cycle may result in discontinuities or motion-related artifacts in a reconstructed image or a rendered volume comprising a sequence of adjacent images. Therefore, in the context of cardiac imaging, it is generally desirable to acquire or select projection data from a common cardiac phase, such as during a phase in which motion is minimized, that is during the diastolic phase.

Figure 3:
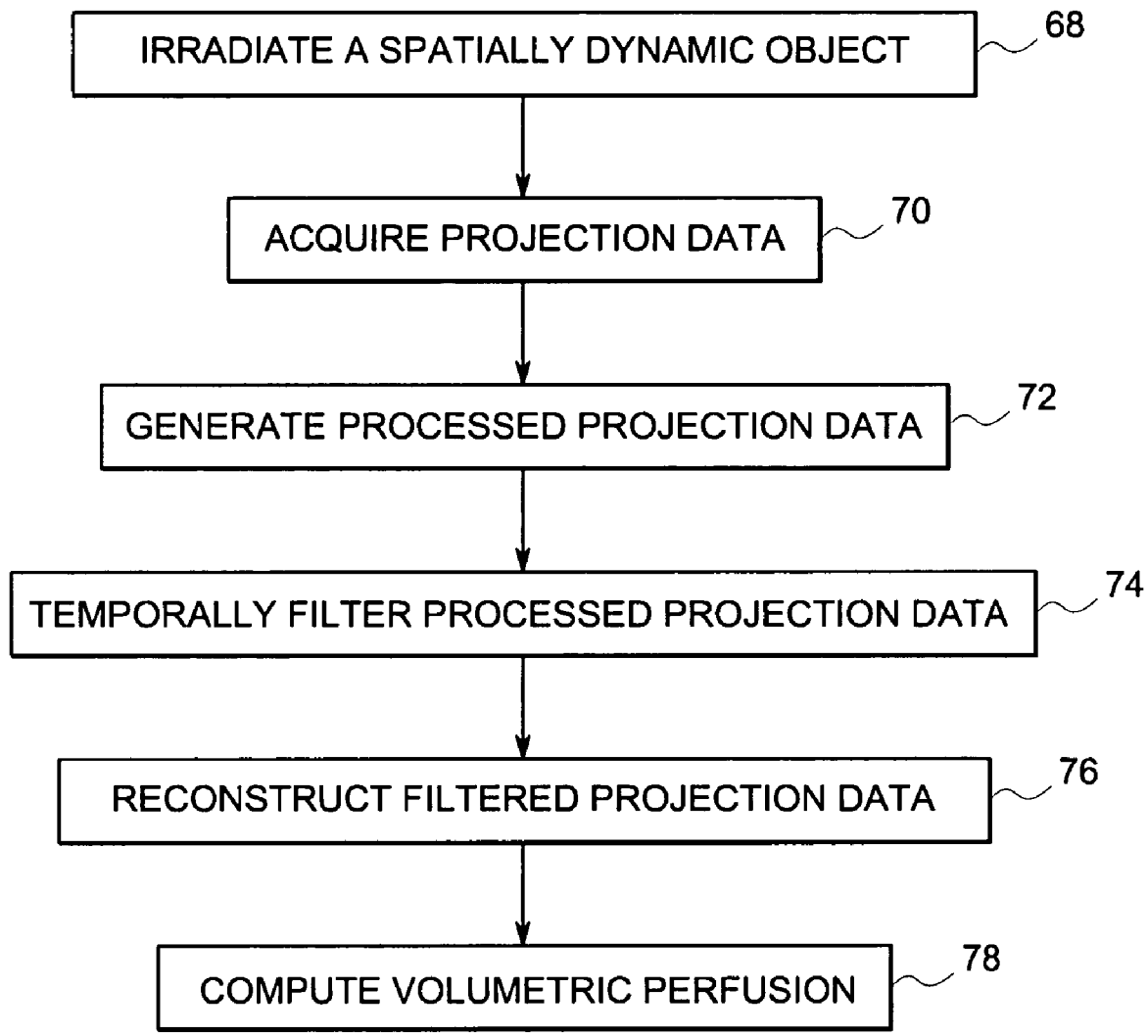
FIG. 3 is a flowchart illustrating a method for computing volumetric perfusion in a spatially dynamic organ using a CT imaging system, in accordance with aspects of the present technique.

According to aspects of the present technique, a method for computing volumetric perfusion in a spatially dynamic object is presented. FIG. 3 depicts a process flow for computing volumetric perfusion in a spatially dynamic object. In one embodiment, the spatially dynamic object may include a spatially dynamic organ, such as the heart. However, as will be appreciated by one skilled in the art, the present technique may be applied to other spatially dynamic organs, such as, but not limited to, the lungs or the colon.

As depicted in FIG. 3, step 68 depicts an initial step in the process of computing volumetric perfusion in a spatially dynamic object. In certain embodiments, the spatially dynamic object may include a spatially dynamic organ, such as the heart. Step 68 includes irradiating the heart, within a field of view of the computed tomography (CT) imaging system for requisite view angle positions of the gantry. In accordance with aspects of the present technique, a contrast enhancing medium may be administered to the patient 18 (see FIG. 1). As will be appreciated by one skilled in the art, the contrast enhancing medium may facilitate the enhancement of contrast between reconstructed images of bodily tissues, such as the heart, that absorbs the contrast enhancing medium at different rates. The contrast enhancing medium is typically a fluid which may be administered to the patient 18 as an intravenous infusion at a steady state to provide a generally steady state of contrast for cardiac CT imaging. Alternatively, for studies such as perfusion studies or contrast intake studies, a bolus injection of the contrast enhancing medium may be administered, where a large quantity of the contrast enhancing medium is rapidly intravenously injected. According to aspects of the present technique, the contrast enhancing medium may be administered to the patient during step 68.

Further, at step 70, the CT imaging system may be operated in a continuous acquisition mode to acquire projection data representative of the heart. Although shown as separate steps, in one embodiment, step 68 and step 70 may occur concurrently as the gantry is rotated. In addition, at step 72, the acquired projection data may be processed to generate processed projection data. For example, in one embodiment of the present technique, the processing step 72 may apply techniques to generate time-resolved projection data. At step 74, the processed projection data may be temporally filtered at each view angle position to generate projection data with improved signal-to-noise ratio, which enables improved estimates of perfusion as well as reduces dose to the patient. It may be noted that step 74 may be optional depending on the signal-to-noise ratio of the acquired data. Further, it may be noted that in one embodiment, steps 72 and 74 may be performed simultaneously by combining steps 72 and 74. Subsequently, at step 76, the temporally filtered projection data or time-resolved projection data if step 74 is omitted, may be employed to generate an ensemble of reconstructions of the spatially dynamic object. The ensemble of reconstructed images may then be employed to compute volumetric perfusion as depicted in step 78. Steps 68–78 will be described in greater detail hereinafter with reference to FIGS. 4 and 5.

Turning now to FIG. 4, an exemplary method for computing volumetric perfusion in a spatially dynamic object, such as the heart, employing a CT imaging system 10 (see FIG. 1) is presented. As depicted in FIG. 4, step 80 illustrates an initial step in the process of computing volumetric perfusion in the heart. Step 80 includes positioning a patient 18 (see FIG. 1) within the imaging field of view of the CT imaging system 10 such that the area detector 22 (see FIG. 1) encompasses the spatially dynamic organ for all view angle positions of the gantry.

In accordance with aspects of the present technique, the spatially dynamic organ, such as the heart, may be positioned between the radiation source 12 (see FIG. 1) and the area detector 22 such that the area detector 22 encompasses the heart within the field of view of the CT imaging system 10 for all view angle positions of the gantry 54 (see FIG. 2). In other words, the area detector 22 encompasses a field of view containing the spatially dynamic heart for all view angle positions of the gantry.

In accordance with further aspects of the present technique, the CT imaging system 10 may be operated in a continuous data acquisition mode such that the sampling frequency of the projection data measuring the uptake and washout of a contrast enhancing medium in the spatially dynamic object at each view position is approximately 1 Hertz when the gantry 54, including the area detector 22, rotates at a speed of approximately 1 rotation per second.

Further, as previously described, in accordance with aspects of the present technique, a contrast enhancing medium may be administered to the patient 18 (see FIG. 1). As will be appreciated by one skilled in the art, the contrast enhancing medium may facilitate the enhancement of contrast between reconstructed images of bodily tissues, such as the heart, that absorb the contrast enhancing medium at different rates. According to aspects of the present technique, the contrast enhancing medium may be administered to the patient subsequent to step 80.

At step 82, the spatially dynamic organ, such as the heart, may be irradiated within a field of view of the CT imaging system for requisite view angle positions of the gantry 54. Typically, the patient may be exposed to radiation in a range from about 5 mSv to about 10 mSv, for example. Subsequently, at step 84, projection data representative of a slab of the spatially dynamic organ may be acquired. In accordance with aspects of the present technique, the projection data representative of the slab of the spatially dynamic organ may be continuously acquired by operating the CT imaging system in a continuous acquisition mode. Typically, the imaging includes acquiring a plurality of projection data relating to axial slices spanning the region of interest, such as the heart, and further spans at least one cardiac cycle period. In one embodiment, steps 82 and 84 may occur simultaneously as the gantry 54 is rotated about patient 18.

As will be appreciated, the projection data may be acquired in the presence of absorbed contrast enhancing medium. The initial sets of projection data acquired during step 84 may be marked by absence of contrast enhancing medium, which may be a result of the contrast enhancing medium being injected subsequent to the initial scanning or may be a result of delayed absorption of the contrast enhancing medium with the injection occurring prior to the initial scanning. These initial sets of acquired projection data may serve as a baseline in order to facilitate the study of contrast dynamics of the region of interest. Contrast dynamics may be defined as the uptake and washout of the contrast enhancing medium over a predetermined period of time, as previously described.

Typically, the subsequent sets of projection data may be acquired in the presence of absorbed contrast enhancing medium. Consequently, with the acquisition of a series of subsequent sets of projection data, the rate of absorption of the contrast enhancing medium at various anatomical regions of interest may be analyzed and employed for various diagnoses.

At step 86, the projection data may be reformatted via a fan-to-parallel rebinning process. Accordingly, fan projections may be resampled into a set of corresponding parallel projections. Subsequently, well-defined parallel-projection reconstruction methods may be applied to the rebinned projection data. Following step 86, the resampled projection data may be processed to generate time-resolved projection data, at step 88.

To avoid the image artifacts associated with cardiac motion, it may be desirable to reconstruct projection data acquired at the same phase into the desired images. This may be done by selective acquisition of the projection data (prospective gating) or by selecting and reconstructing only projection data acquired at the same cardiac phase (retrospective gating). Such gating techniques may utilize a simultaneously acquired electrocardiogram (ECG) signal that is used to select projection data, either prospectively or retrospectively, at a common phase of the cardiac cycle.

Accordingly, at step 88, the acquired projection data, representative of the spatially dynamic organ, may be employed to retrospectively identify projection data within the same temporal window of motion to be imaged. Typically, in the case of acquisition of cardiac projection data, the ECG signal is measured while acquiring the projection data. However, other methods have been reported that allow generation of a motion detection signal from the projection data themselves. The cardiac projection data may then be retrospectively identified by using the temporal correspondence between the ECG signal and the dependent acquired projection data, to select and reconstruct only that projection data corresponding to a predetermined point in time in the cardiac cycle. For instance, the predetermined point in time in the ECG signal may correspond to a point in time in the cardiac cycle when the heart is substantially stationary. In other embodiments, the extracted signal may be used exclusively to select the projection data at a particular point of the cardiac cycle.

The time-resolved projection data produced as a result of step 88 may then be temporally filtered at each view angle position to reduce noise in the projection data in step 90. It may be noted that step 90 may be optional depending on the signal-to-noise ratio of the measured projection data. In one embodiment, the temporal filtering may include filtering the acquired projection data at a selected frequency range. Further, in another embodiment, a Butterworth filter may be employed to facilitate the filtering of the time-resolved projection data. Further, it may be noted that in one embodiment, steps 88 and 90 may be performed simultaneously by combining steps 88 and 90.

Processing the rebinned data to generate time-resolved projection data may facilitate computation of volumetric perfusion measurements that include an enhanced temporal resolution in the reconstruction of contrast dynamics. Additionally, temporally filtering the time-resolved data may also result in an increased signal-to-noise ratio thereby advantageously enhancing the image quality in reconstructed images. A further advantage of temporally filtering the rebinned data is that the radiation dose applied during imaging may be reduced as the same image quality may be achieved with projection data acquired with poorer signal-to-noise ratio. By reducing the dose administered to the patient, the signal-to-noise ratio in the perfusion measurements is reduced if unfiltered projection data is used to reconstruct images; however, image quality is not sacrificed employing the filtering techniques described herein.

Subsequently, at step 92, the temporally filtered projection data or time-resolved projection data if step 90 is omitted, may be employed to generate an ensemble of reconstructions that depict the contrast dynamics of the spatially dynamic organ, such as the heart. At step 94, volumetric perfusion parameters representative of the spatially dynamic organ may then be computed from the reconstructed images.

Referring to FIG. 5, an exemplary method for computing volumetric perfusion in a spatially dynamic object, such as the heart, employing a CT imaging system 10 (see FIG. 1) is presented. As depicted in FIG. 5, step 96 illustrates an initial step in the process of computing volumetric perfusion in the heart. As described with reference to FIG. 4, step 96 includes positioning a patient 18 (see FIG. 1) within a field of view of the CT imaging system 10 such that the area detector 22 (see FIG. 1) encompasses the spatially dynamic organ for all view angle positions of the gantry 54 (see FIG. 2). Furthermore, at step 98, the spatially dynamic organ, such as the heart, may be irradiated within a field of view of the CT imaging system 10 for requisite view angle positions of the gantry 54, as previously described.

Subsequently, at step 100, projection data representative of a slab of the spatially dynamic organ may be acquired. In accordance with aspects of the present technique, the projection data representative of the slab of the spatially dynamic organ may be acquired by operating the CT imaging system 10 in a continuous data acquisition mode, as previously described. Additionally, the projection data may be acquired in response to an external trigger. For example, the external trigger that may be employed to acquire cardiac projection data may include an ECG signal. Also, during the acquisition of lung projection data, a signal generated by the device employed to measure lung volume may be employed as the external trigger. In other words, for an organ of interest, an optical signal, a mechanical signal, an electrical signal, or any other signal representative of the motion of the organ of interest may be employed to trigger the acquisition of projection data. Additionally, in one embodiment, to reduce the radiation dose to the patient, steps 98 and 100 may occur simultaneously as a result of the external trigger.

Further, in one embodiment, projection data, acquired at an offset of 70% of a cardiac period from each maximum of the ECG waveform is selected for reconstruction. In addition, the projection data within the same temporal window of cyclic motion of the organ of interest to be imaged may be acquired at a predetermined sampling rate that may be required to capture the contrast dynamics in the organ of interest. Also, the speed of the gantry rotation and the reconstruction algorithm may be chosen to achieve substantially high temporal resolution in the reconstructed images. For example, well-known sector reconstruction algorithms may be applied to improve temporal resolution in data used for image reconstruction.

In one embodiment, since the view angle positions change for each acquisition, the acquired projection data may be resampled via a fan-to-parallel rebinning step. Alternatively, if it is feasible to acquire the projection data for each acquisition at the same angular positions, the fan-to-parallel rebinning step may be omitted.

Further, as previously described, the acquired projection data, representative of the spatially dynamic organ, may be employed to retrospectively identify projection data within the same temporal window of motion to be imaged, at step 102. As previously noted, generating time-resolved projection data may facilitate computation of volumetric perfusion measurements that include an enhanced temporal resolution in the reconstruction of contrast dynamics.

Subsequently, at step 104, the projection data may be temporally filtered to facilitate reduction of noise in the measurements. In one embodiment, step 104 may be optional depending on the signal-to-noise ratio of the measured projection data. As previously described, temporally filtering time-resolved data may result in an increased signal-to-noise ratio thereby advantageously enhancing the image quality in reconstructed images. Further, it may be noted that in one embodiment, steps 102 and 104 may be performed simultaneously by combining steps 102 and 104.

Following step 104, the temporally filtered data or time-resolved projection data if step 104 is omitted, may be utilized to reconstruct an ensemble of images at step 106. The reconstructed ensemble of images may then be employed for perfusion assessment at step 108, as previously described.

Furthermore, in certain embodiments, it may be desirable to selectively reduce noise in the reconstructed images to advantageously enhance the assessment of perfusion parameters. Filtering techniques may be applied to the ensemble of reconstructed images to facilitate the reduction of noise in the reconstructed images. Furthermore, as will be appreciated, artifacts in the reconstructed images may also be attributable to translational or rotational motion experienced by the spatially dynamic organ during the scan interval. For example, artifacts in the reconstructed images of the colon may be a consequence of peristalsis. Also, motion experienced by the liver as a result of respiratory motion may result in artifacts in the reconstructed images of the liver. Consequently, in certain embodiments, image domain registration techniques, such as phase registration or phase selection from a cardiac dataset reconstructed over multiple phases of the cardiac cycle, may be applied to the projection data prior to the application of the temporal filtering techniques to beneficially reduce artifacts in the reconstructed images of spatially dynamic organs.

Moreover, the techniques described hereinabove advantageously permit a reduction in dose of radiation for a comparable slice thickness used for the assessment of perfusion parameters. Alternatively, the techniques described hereinabove would facilitate perfusion assessment in thinner slices at the same radiation dose. For example, the techniques described hereinabove may facilitate perfusion assessment in slices having a thickness of about 1.25 mm.

As mentioned previously, using the concurrently acquired ECG signal is one method to assist in retrospective selection of projection data at a certain phase of the cardiac cycle; however, as is known in the art, information extracted from the projection data itself may be used to estimate the cardiac phase of the acquired projection data. With continued reference to cardiac projection data, the different periods of the cardiac cycle, such as diastole and systole, may be related to corresponding inflections, maxima, minima, or crossings within the extracted waveform or signal such that one or more phases of interest may be determined from the projection data. In this manner, only that image data acquired at the desired phase or phases of interest may be reconstructed to generate a cardiac image, thereby reducing or eliminating artifacts attributable to cardiac motion. For example, in one embodiment, the volume of the heart may be reconstructed using projection data acquired at a derived inflection point, minima, maxima, or crossing or at some interval or percentage of a cardiac period from such a point in the extracted signal. Other methods of determining phase information also exist, such as using data concurrently acquired by using other sensors or imaging modalities, such as ultrasound. These methods are also useful for rejecting projection data relating to arrhythmias, and the like.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for computing volumetric perfusion using a computed tomography imaging system, the method comprising:
   irradiating a spatially dynamic object within a field of view of the computed tomography imaging system for requisite view angle positions of the gantry;
   operating the computed tomography imaging system in a continuous data acquisition mode to acquire projection data representative of the spatially dynamic object;
   processing the projection data to generate time-resolved projection data;
   generating reconstructions using the time-resolved projection data; and
   computing the volumetric perfusion in the spatially dynamic object using the reconstructed data.

2. The method of claim 1, comprising temporally filtering the time-resolved data at the requisite view angle positions to generate filtered projection data.

3. The method of claim 2, wherein the step of processing and the step of temporally filtering are performed simultaneously.

4. The method of claim 1, wherein the spatially dynamic object comprises an organ.

5. The method of claim 1, comprising measuring an uptake and washout of a contrast enhancing medium in the spatially dynamic object as captured by the projection data acquired at requisite view angle positions of the gantry.

6. The method of claim 1, comprising identifying projection data at requisite view angle positions of the gantry corresponding to a predetermined temporal window of cyclic motion of the spatially dynamic object.

7. The method of claim 6, further comprising resampling the projection data by performing a fan-to-parallel rebinning process.

8. The method of claim 1, comprising acquiring the projection data in response to an external trigger.

9. The method of claim 8, wherein the external trigger comprises an electrocardiogram signal.

10. A computed tomography imaging system for computing volumetric perfusion in a spatially dynamic object, the system comprising:
    a radiation source;
    an area detector; and
    a computer operationally coupled to the radiation source and the area detector, wherein the computer is configured to:
        irradiate a spatially dynamic object within a field of view of the computed tomography imaging system for requisite view angles;
        operate the computed tomography imaging system in a continuous data acquisition mode to acquire projection data representative of the spatially dynamic object;
        process the projection data to generate time-resolved projection data;
        generate reconstructions using the time-resolved projection data; and
        compute the volumetric perfusion in the spatially dynamic object using the reconstructed data.

11. The computed tomography imaging system of claim 10, wherein the computer is configured to temporally filter the time-resolved data at the requisite view angle positions to generate filtered projection data.

12. The computed tomography imaging system of claim 11, wherein the computer is configured to simultaneously perform the step of processing and the step of temporally filtering.

13. The computed tomography imaging system of claim 10, wherein the computer is configured to acquire the projection data in response to an external trigger.

14. The computed tomography imaging system of claim 10, wherein the computer is configured to measure an uptake and washout of a contrast enhancing medium introduced into the spatially dynamic object as captured by the projection data measured at the requisite view angle positions of the gantry.

15. The computed tomography imaging system of claim 10, wherein the computer is configured to identify projection data at the requisite view angle positions corresponding to a predetermined temporal window of cyclic motion of the spatially dynamic object.

16. The computed tomography imaging system of claim 10, wherein the computer is configured to perform a fan-to-parallel rebinning process to resample the projection data.

17. A computer readable medium, comprising:
  code adapted to irradiate a spatially dynamic object within a field of view of the computed tomography imaging system for requisite view angle positions of the gantry;
  code adapted to operate the computed tomography imaging system in a continuous data acquisition mode to acquire projection data representative of the spatially dynamic object;
  code adapted to process the projection data to generate time-resolved projection data;
  code adapted to generate reconstructions using the time-resolved projection data; and
  code adapted to compute the volumetric perfusion in the spatially dynamic object using the reconstructed data.

18. The computer readable medium of claim 17, comprising code adapted to temporally filter the time-resolved data at the requisite view angle positions to generate filtered projection data.

19. A method for computing volumetric perfusion using a computed tomography imaging system, the method comprising:
  irradiating a spatially dynamic object within a field of view of the computed tomography imaging system for requisite view angle positions of the gantry;
  operating the computed tomography imaging system in a continuous data acquisition mode to acquire projection data representative of the spatially dynamic object;
  identifying projection data corresponding to a predetermined temporal window of cyclic motion of the spatially dynamic object;
  performing a fan-to-parallel rebinning of the identified projection data to generate resampled projection data;
  processing the resampled projection data to generate time-resolved projection data;
  generating reconstructions using the time-resolved projection data; and
  computing the volumetric perfusion in the spatially dynamic object using the reconstructed data.

20. The method of claim 19, comprising temporally filtering the time-resolved projection data at the requisite view angle positions to create filtered projection data.

21. The method of claim 19, comprising measuring an uptake and washout of a contrast enhancing medium in the spatially dynamic object as captured by the projection data measured at the requisite view angle positions of the gantry.

22. A method for computing volumetric perfusion using a computed tomography imaging system, the method comprising:
  irradiating a spatially dynamic object within a field of view of the computed tomography imaging system for requisite view angle positions of the gantry;
  operating the computed tomography imaging system in a continuous data mode to acquire projection data representative of the spatially dynamic object responsive to an external trigger;
  processing the projection data to generate time-resolved projection data;
  generating reconstructions using the time-resolved projection data; and
  computing the volumetric perfusion in the spatially dynamic object using the reconstructed data.

23. The method of claim 22, comprising temporally filtering the time-resolved projection data at the requisite view angle positions of the gantry to create filtered projection data.

24. The method of claim 22, comprising performing a fan-to-parallel rebinning to resample the projection data prior to the step of processing the projection data to generate time-resolved projection data.

* * * * *